(12) United States Patent
Vaddadi et al.

(10) Patent No.: US 12,417,820 B2
(45) Date of Patent: Sep. 16, 2025

(54) METHOD AND SYSTEM FOR MAPPING READ SEQUENCES USING A PANGENOME REFERENCE

(71) Applicant: Tata Consultancy Services Limited, Mumbai (IN)

(72) Inventors: Kavya Naga Sai Vaddadi, Hyderabad (IN); Naveen Sivadasan, Hyderabad (IN); Rajgopal Srinivasan, Hyderabad (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 953 days.

(21) Appl. No.: 17/593,240

(22) PCT Filed: Mar. 13, 2020

(86) PCT No.: PCT/IB2020/052294
§ 371 (c)(1),
(2) Date: Sep. 13, 2021

(87) PCT Pub. No.: WO2020/183428
PCT Pub. Date: Sep. 17, 2020

(65) Prior Publication Data
US 2022/0157401 A1 May 19, 2022

(30) Foreign Application Priority Data
Mar. 14, 2019 (IN) .............................. 201921010012

(51) Int. Cl.
G16B 30/10 (2019.01)
G16B 40/30 (2019.01)
(52) U.S. Cl.
CPC ............. G16B 30/10 (2019.02); G16B 40/30 (2019.02)

(58) Field of Classification Search
CPC ................................ G16B 30/10; G16B 40/30
See application file for complete search history.

(56) References Cited

U.S. PATENT DOCUMENTS

2017/0199960 A1  7/2017  Ghose et al.
2018/0373839 A1  12/2018  Semenyuk

OTHER PUBLICATIONS

Paten, Benedict, et al. "Genome graphs and the evolution of genome inference." Genome research 27.5 (2017): 665-676. (Year: 2017).*

(Continued)

Primary Examiner — Olivia M. Wise
Assistant Examiner — Mary C Leverett
(74) Attorney, Agent, or Firm — Finnegan, Henderson, Farabow, Garrett & Dunner, LLP

(57) ABSTRACT

There is a demand for low-cost efficient robust method for mapping read sequences with genome variation graph in genomic study. This disclosure herein relates to a method and system for mapping read sequences with genome variation graph by constructing a subgraph using a novel combination of graph embedding and graph winnowing techniques. The system processes the obtained plurality of read sequences and a genome variation graph for constructing the subgraph by computing an embedding for the genome variation graph utilizing a graph embedding technique. Further, graph index is generated for the genome variation graph based on the embedding and the genome variation graph utilizing the graph winnowing technique. Then computes gapped alignment score for read sequence (r) with its corresponding subgraph. Thus, enables a reliable method for read sequence with accurate, memory efficient and scalable system for mapping read sequences with genome variation graph.

14 Claims, 8 Drawing Sheets

(56) References Cited

OTHER PUBLICATIONS

Garrison, Erik, et al., "Variation graph toolkit improves read mapping by representing genetic variation in the reference", Nature Biotechnology, 2018, vol. 36 (9), pp. 875-879, Nature Research, https://www.researchgate.net/publication/345695333_Sequence_variation_aware_genome_references_and_read_mapping_with_the_variation_graph_toolkit/link/6003416892851c13fe7e77a/download.

Li, Heng, "Minimap and miniasm: Fast Mapping And De Novo Assembly For Noisy Long Sequences", *Bioinformatics*, Jul. 2016, vol. 32, Issue 4, pp. 2103-2110, Oxford Academic https://watermark.silverchair.com/btw152pdf?token-AQECAHi208BE49Ooan9kkh-jWErcy7Dm3ZL.9013af.KAc485ysqAAAuEwggLdBgkqhkiG9wOBBwaoQLOMIICvglBADCCA&MGOSqGSIb3DOEHATAeBolahkgBZQMEAS4WEQOMBIHSG-B88YrFoM8MAGEQqlICIAUYSr2FcKy2NJorS-O1n12MTGTkrNBE5x-M7HDJPSqdKGEwTovIKcMh:6:4KZHo2HSUeAGAbQ. IN2NAbhanRaA015VpCBPJ-VShQICArz_7bn5eW5R4imaw00fU XhyGhbIWVRPoiNruYI709wPWGckaYAsSQ8aw9H0-x0Y2gOGX-. XaYIW060aEZOAY XmumszWiaPQZnp2RuoGOfkC8x12ahAphf LsObforsiKRFL014npB9lxnPHRTIO4vPOtoiTyVWO7uspiXCGD T5BrrrbPitiQKHLOI-V3DVA orgNlimOzGXnvJegHmmwY-RoRBLuEz9k k5nrJligbicvK2VXHOUx5nyk18aldwgVpFV8yEntL 5AV3YkcOhorIWnXNGQIDWB_Olocitym9181078N81Pc AfLv8no: EFcW7CZ7dElueLD6XKbHve_ED:OmJE0403QyYwly mpLTu2Zi7mKISAW4vUskPtGvwV8zCGLIAsQGeF7xxIN9cleilN dlianTQJlidlavx3HXGTBCDJJJJJ7169vn1aa738YFe3HHqKCQuo QodGn9WHcGH1KOBC8vbUmFtoit PqYLwsJNEcSzUmM9INO TnbJOQUC6dW7xezYNC9oftacZOQBDULFhYTL9kKVIFnKCM aZd6XsoGGDHCOELPnakc7ph diBvUifrelKaADE608x3c8-OHTomyh9Sc9_K4ia8MsZ3z:Od0mVe2wHOOwSKZ ZOSACVBgQsu-Ae0Q2oitXN4 Scoy9gzz2CdO_GyQVCy R7iA26DCVJVCkiBEdpf0GInkUGTUnW5xz4alwPEsQ a1BUD8vVGSIDoPH-6Wpr9byEArD2Q.

DU 1, Jingcheng et al., "Gene2vec: distributed representation of genes based on co-expression", BMC Genomics, 2019, vol. 20, NCBI, https://www.ncbi.nim.nih.gov/omc/articles/PMC6360648/pdf/12864_2018_Article_5370.pdf.

Marcais, Guillaume et al., "Improving the performance of minimizers and winnowing scheme" Title of the item: Bioinformatics, Jul. 2017, vol. 33, Issue: 14, pp. i110-i117, Oxford Academic, https://watermark.silverchair.com/btx235.pdf?token= AQECAHi208BE49Ooan9kkhW_Ercy7Dm3ZL_9Cf3qfKAc485ys gAAAuEwggLdBgkqhkiG9w0BBwagggLOMIICygIBADCCAsM GCSqGSIb3DQEHATAeBglghkgBZQMEAS4wEQQMbpFGaYN QmfsenMJKAgEQglICIJjv06PQwwg-3owmQldShmv5M-YT2bsHjSni_uTaQ_yu2KZzNP3p7pyr30J6m_17h55X9 OH015zu7uPKlbk2CSXygpztGLpoiRq_V982-2UAueRp v7hLrSbmpuqs2omT4qwvNWwsuHDdlrwa8FMf8pWTkhl_ yYrYOW_jcZEfHRK0KGkrvS1R-5rsnkl5hCdKkbG6EM5ZMFjQ C8SLwRR9qWquVT6BXVwYGxs3if57xyWa8dX2QbaUDF5zhxk SrLKJhtA2Fz-mrn7fdAcK2y7uO1dNoFbFxaRaMpAlabzjNuFi28rt Ypk8jSjDUBsdK5PE9M1ID-ewqB_uDq1JV5KR6yoSt5qH Q69qsh5INOVURC3-yUimYTipxqPzbBjA-PWhnENkEarC-pX1QmxmfymjDc20gWFXFL4uVcWXOGVzVyDs-IUd6Z lauWR5kpPCyrDkel_JdT3ftLca60989x5-nopb5503C2hkMp HMOX2W2hJ_D0m8Hyubib10T8jVVG4cu4L8m-uq4OHS 13SFBxPRHHj9G3wiM-miBd4yweuOWu750goattFJ9P5zZJ LCmE5gXLvktv3q9YMVC0Tq_yON8oyVekFGXuvfauA8Rh6E0882_ E2byXhw2ZBv1CrbXYBB9_RHvLmx8un7DZ5NXgAFLxqTeZ D4MEIs4ldUluVdaDI3-e0jtjV17b4HozlFdEq4ErSlxESnnJxTZ3sN nE93XTEzrpHrax0aj7x61u_DgMuf3u8pTSUO10BvOxqLgiMk9D HUKxF3iEEO0xMicvcnRXyhq018PEtzpJBMP_gxiLtBOE L1LynWuiyWZjCkfPPHGAXDHYaSk6BALEnb6XR U4uQp8x7P81p9wBBX60MUqv0PuA.

Jain, Chirag et al., "A Fast Approximate Algorithm for Mapping Long Reads to Large Reference Databases", Bioinformatics, 2018, vol. 25 (7), pp. 766-779, NCBI, https://www.ncbi.nlm.nih.gov/pmc/articles/PMC6067103/pdf/cmb.2018.0036.pdf.

Kavya, V. et al., "Read Mapping on Genome Variation Graphs", Computer Science, 2019, Semantic Scholar, https:/drops.dagstuhl.de/opus/volltexte/2019/11037/pdf/LIPIcs-WABI-2019-7.pdf.

International Search Report for International Application No. PCT/IB20/52294 mailed Aug. 31, 2020.

Written Opinion of the International Searching Authority for International Application No. PCT/IB20/52294 mailed Aug. 31, 2020.

\* cited by examiner

METHOD AND SYSTEM FOR MAPPING READ SEQUENCES USING A PANGENOME REFERENCE

CROSS-REFERENCE TO RELATED APPLICATIONS AND PRIORITY

This present application is a U.S. National Stage Filing under 35 U.S.C. § 371 and claims priority from International Application No. PCT/IB2020/052294 filed on Mar. 13, 2020, which application claims priority under 35 U.S.C. § 119 from India Application No. 201921010012 filed on Mar. 14, 2019. The entire contents of the aforementioned application are incorporated herein by reference.

TECHNICAL FIELD

The disclosure herein generally relates to the field of pangenome collection, and, more particularly, to method and system for mapping read sequences using a pangenome reference.

BACKGROUND

Genome study provides potential traits of genetical information about life and health of human beings. Conventionally, high quality genome references are widely used for read sequence alignment and variation analysis. Improved analysis is possible with pangenome reference collection. Genome variation graphs are natural candidates to represent pangenome collection. In such genome variation graphs, common subsequences are encoded as vertices and the genomic variations are captured by introducing additional labeled vertices and directed edges. The non-linear graph structure has challenges to the fundamental problems of sequence alignment and read mapping. However, a scalable and an efficient pangenome based analysis pipeline is necessary for replacing linear reference with graph structured genomes for obtaining improved performance.

In conventional methods, genome analysis primarily relies on linear references. These methods map sequence reads to a reference from the genome collection by treating each reference sequence in the collection separately. However, these methods are time consuming and memory intensive which requires high volume of RAM memory and disk space. In some existing approaches such as RNA sequential analysis based on transcript reference collection, estimating transcript abundance and identifying transcript variations using the collection of linear transcript sequences as reference is time consuming. Also, in another method for achieving high throughput, mapping algorithms restrict gapped alignment only on small regions of the reference where read sequences can align optimally. However, these conventional methods limits in mapping read sequences accurately and efficiently by aligning each read to a relevant portion of each of the reference genome from the collection. The existing methods also limits in handling massive size of non-linear structure of the reference genome variation graphs for higher throughput and scalability.

SUMMARY

Embodiments of the present disclosure present technological improvements as solutions to one or more of the above-mentioned technical problems recognized by the inventors in conventional systems. For example, in one embodiment, a system for is provided. The system includes a processor, an Input/output (I/O) interface and a memory coupled to the processor is capable of executing programmed instructions stored in the processor in the memory to obtain, a plurality of read sequences (r) and a genome variation graph (G), wherein the genome variation graph is a representation of pangenome collection which includes a vertex set (V) and an edge set (E). Further, an embedding ($\lambda$) is generated for the genome variation graph (G) utilizing a graph embedding technique. Then, a graph index ($I_G$) is generated for the genome variation graph (G) based on the embedding ($\lambda$) and the genome variation graph (G) utilizing a graph winnowing technique. Further, iteratively mapping each read sequence to genome variation graph by constructing a subgraph for each read sequence (r) using the variation map index, wherein the variation map index comprises a list of the graph index ($I_G$) and the genome variation graph (G). Furthermore, an alignment score for read sequence (r) with its corresponding subgraph.

In one embodiment, generating the embedding ($\lambda$) for the genome variation graph (G) utilizing the graph embedding technique comprises extracting, each entity (v) from the vertex set (V), the edge set (E), a vertex label $\ell$ (v) for each entity(v) and a graph coordinate (v,i), where i is the offset for vertex label $\ell$ (v) from the genome variation graph (G). Further, an auxiliary undirected weighted graph (G') is created using the genome variation graph (G) by, including, a pair of vertices for each entity (v) of the vertex set (V) in the genome variation graph (G), wherein each pair of vertices includes a first element and a second element of the entity (v). Further, the first element and the second element of each entity (v) is connected with an undirected edge length of weight I decremented with a predefined value, wherein l is the length of the vertex label $\ell$ (v) in the genome variation graph (G). For every entity (e) of the edge set (E), the second element of source vertex is fastened with the first element of destination vertex of the genome variation graph (G) with a weight. The shortest path is computed from the source vertex to the available vertices of the auxiliary undirected weighted graph (G'), wherein the source vertex is identified based on the first element having zero incoming edges in the genome variation graph (G) and an embedding ($\lambda$) is generated for the graph coordinates where the distances between the graph coordinates are based on the shortest path distances of the graph coordinates where the shortest path distance for each graph coordinate (v,i) of the genome variation graph (G) is based on the minimized shortest path distance to the first element and the second element of the vertex set (V) in the auxiliary undirected weighted graph (G').

In another embodiment, the graph index ($I_G$) for the genome variation graph (G) is generated based on the embedding ($\lambda$) and the genome variation graph (G) utilizing the graph winnowing technique comprises for obtaining, a plurality of sequence winnow ($S_w$) paths for the genome variation graph (G) using a winnow length (w). The path label for each path of the sequence winnow ($S_w$) is extracted by concatenating the vertex labels along the path based on the winnow length (w). Further, a sequence winnowing ($h_w$) for each path label is computed based on the elements of the minimizer graph coordinates. Further, a set of distinct minimizer graph coordinates ($H_w$) is generated by performing sequence winnowing ($h_w$) for each path and the graph index ($I_G$) is generated using the elements of the minimizer graph coordinates in ($H_w$) the embedding ($\lambda$) and a dictionary key (k).

In another aspect, provides a method that includes a processor, an Input/output (1/O) interface and a memory coupled to the processor is capable of executing programmed instructions stored in the processor in the memory to obtain, a plurality of read sequences (r) and a genome variation graph (G), wherein the genome variation graph is a representation of pangenome collection which includes a vertex set (V) and an edge set (E). Further, an embedding (λ) is generated for the genome variation graph (G) utilizing a graph embedding technique. Then, a graph index ($I_G$) is generated for the genome variation graph (G) based on the embedding (λ) and the genome variation graph (G) utilizing a graph winnowing technique. Further, iteratively mapping each read sequence to genome variation graph by constructing a subgraph for each read sequence (r) using the variation map index, wherein the variation map index comprises a list of the graph index ($I_G$) and the genome variation graph (G). Furthermore, an alignment score for read sequence (r) with its corresponding subgraph.

In one embodiment, generating the embedding (λ) for the genome variation graph (G) utilizing the graph embedding technique comprises, extracting, the vertex set (V), the edge set (E), a vertex label (l) and a graph coordinate (v,i), where i is the offset for vertex label (l) from the genome variation graph (G). Further, an auxiliary undirected weighted graph (G') is created using the genome variation graph (G) by including, a pair of vertices for each vertex (v) in the genome variation graph (G), wherein each pair of vertices includes a first element and a second element of the vertex (v). Further, the first element of the vertex (v) and the second element of the vertex (v) is connected with an undirected edge length of weight $\ell$ (v) decremented with a predefined value, wherein l is the label length of the vertex (v) in the genome variation graph (G). Further, for every edge set (E), the second element of source vertex (v) is fastened with the first element of destination vertex (v) of the genome variation graph (G) with a weight. Then, the shortest path is computed from source vertex to the available vertices of the auxiliary undirected weighted graph (G'), wherein the source vertex is identified based on the first element having zero incoming edges in the genome variation graph (G) and an embedding (λ) for each graph coordinate (v,i) of the genome variation graph (G) is generated based on the shortest path and the first element, second element of the vertex set in the auxiliary undirected weighted graph (G').

In another embodiment, the graph index ($I_G$) for the genome variation graph (G) is generated based on the embedding (λ) and the genome variation graph (G) utilizing the graph winnowing technique comprises for obtaining, a plurality of sequence winnow ($S_w$) paths for the genome variation graph (G) using a winnow length (w). The path label for each path of the sequence winnow ($S_w$) is extracted by concatenating the vertex labels along the path based on the winnow length (w). Further, a sequence winnowing ($h_w$) for each path label is computed based on the elements of the minimizer graph coordinates. Further, a set of distinct minimizer graph coordinates ($H_w$) is generated by performing sequence winnowing ($h_w$) for each path and the graph index ($I_G$) is generated using the elements of the minimizer graph coordinates in ($H_w$) the embedding (λ) and a dictionary key (k).

In yet another aspect, provides one or more non-transitory machine-readable information storage mediums comprising one or more instructions, which when executed by one or more hardware processors perform actions includes to obtain, a plurality of read sequences (r) and a genome variation graph (G), wherein the genome variation graph is a representation of pangenome collection which includes a vertex set (V) and an edge set (E). Further, an embedding (λ) is generated for the genome variation graph (G) utilizing a graph embedding technique. Then, a graph index ($I_G$) is generated for the genome variation graph (G) based on the embedding (λ) and the genome variation graph (G) utilizing a graph winnowing technique. Further, iteratively mapping each read sequence to genome variation graph by constructing a subgraph for each read sequence (r) using the variation map index, wherein the variation map index comprises a list of the graph index ($I_G$) and the genome variation graph (G). Furthermore, an alignment score for read sequence (r) with its corresponding subgraph.

In one embodiment, generating the embedding (λ) for the genome variation graph (G) utilizing the graph embedding technique comprises, extracting, the vertex set (V), the edge set (E), a vertex label (l) and a graph coordinate (v,i), where i is the offset for vertex label (l) from the genome variation graph (G). Further, an auxiliary undirected weighted graph (G') is created using the genome variation graph (G) by including, a pair of vertices for each vertex (v) in the genome variation graph (G), wherein each pair of vertices includes a first element and a second element of the vertex (v). Further, the first element of the vertex (v) and the second element of the vertex (v) is connected with an undirected edge length of weight $\ell$ (v) decremented with a predefined value, wherein l is the label length of the vertex (v) in the genome variation graph (G). Further, for every edge set (E), the second element of source vertex (v) is fastened with the first element of destination vertex (v) of the genome variation graph (G) with a weight. Then, the shortest path is computed from source vertex to the available vertices of the auxiliary undirected weighted graph (G'), wherein the source vertex is identified based on the first element having zero incoming edges in the genome variation graph (G) and an embedding (λ) for each graph coordinate (v,i) of the genome variation graph (G) is generated based on the shortest path and the first element, second element of the vertex set in the auxiliary undirected weighted graph (G').

In another embodiment, the graph index ($I_G$) for the genome variation graph (G) is generated based on the embedding (λ) and the genome variation graph (G) utilizing the graph winnowing technique comprises for obtaining, a plurality of sequence winnow ($S_w$) paths for the genome variation graph (G) using a winnow length (w). The path label for each path of the sequence winnow ($S_w$) is extracted by concatenating the vertex labels along the path based on the winnow length (w). Further, a sequence winnowing ($h_w$) for each path label is computed based on the elements of the minimizer graph coordinates. Further, a set of distinct minimizer graph coordinates ($H_w$) is generated by performing sequence winnowing ($h_w$) for each path and the graph index ($I_G$) is generated using the elements of the minimizer graph coordinates in ($H_w$) the embedding (λ) and a dictionary key (k).

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
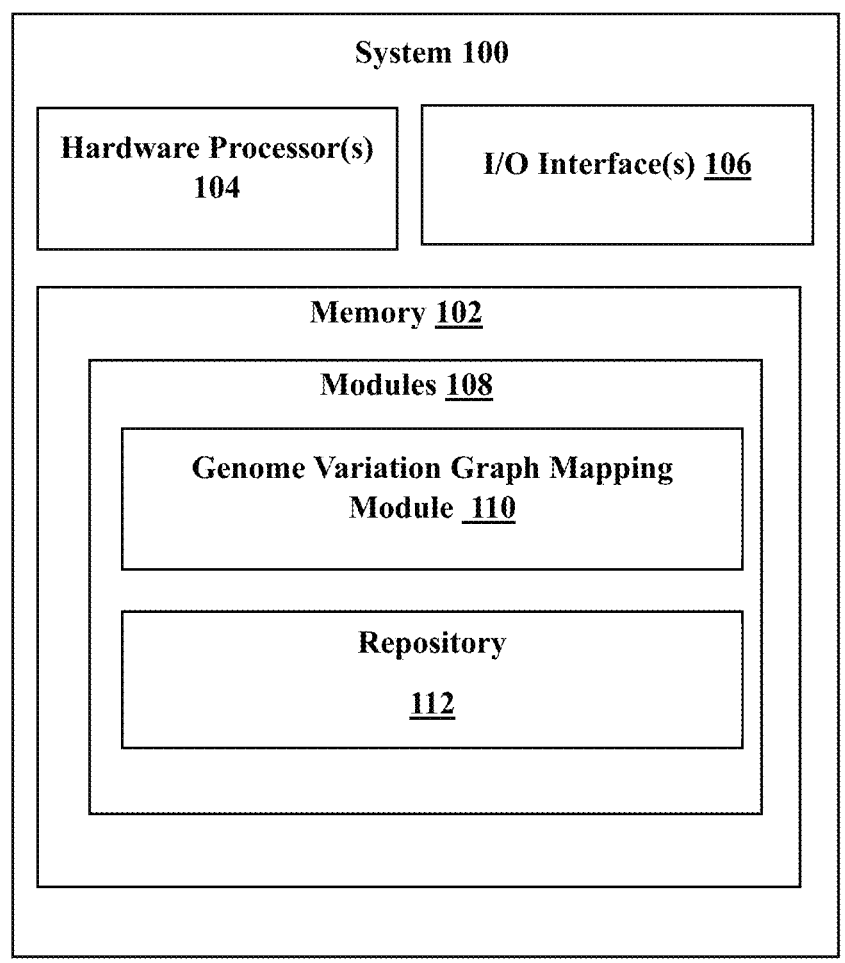
FIG. 1 illustrates an exemplary block of a system, for mapping read sequences using a pangenome reference, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provide a method and a system, for mapping read sequences using a pangenome reference. The disclosed method is an efficient, accurate and scalable system for mapping read sequences using a pangenome reference by constructing a genome variation graph. The method enables to create a space efficient index using locality sensitive minimizer signatures computed using a combined novel approach of a graph winnowing technique and a graph embedding technique for fast and accurate mapping. The proposed disclosure efficiently maps read sequences with genome variation graph by performing gapped alignment using a variation map technique for construction of subgraph for optimal read alignment. This disclosure provides a possible reliable method for alignment of the read sequence (r) through some path in the graph. This method identifies the subgraphs in a qualitative way for both long and short read sequences. This further resulted in significantly smaller graph sizes, that reduces time for gapped alignment of the read sequences to the corresponding identified subgraphs. An example of the said system is described with experiments that involves construction of subgraph from the genome variation graph which is constructed from genome data obtained from various external sources. The proposed disclosure enables in providing a memory efficient, accurate and a scalable framework. Moreover, the disclosure variation map results in enhancing the performance explicitly for long read sequences. However, the disclosed system is further explained with the novel method as described in conjunction with FIG. 1 to 6C below.

Glossary

Path—Sequence of vertices in which each pair of successive vertices are connected by an edge.

Cycle—path that starts and ends on the same vertex.

Weighted graph: Graph in which edges have a weight.

Unweighted graph: Graph in which edges have no weight.

Undirected Graphs: Graph in which each edge can be traversed in either direction.

Directed Graphs: Graph in which each edge can be traversed only in a specified direction.

Cyclic graph: Graph which contains cycles.

Acyclic graph: Graph which contains no cycles.

Subgraph: Graph whose vertices are subset of a given graph and retains edges only between these subset of vertices.

Sorting: Sorting refers to ordering data in an increasing or decreasing fashion according to some linear relationship among the data items.

Skip list: A skip list is a data structure that is used for storing a sorted list of data items that connect increasingly sparse collection of data items.

Array: array is a data structure in computer science which maintains a collection of similar data items.

Hash/Hashing: A hash is a function that converts one value to another. Hashing data is a common practice in computer science and is used for several different purposes.

Locality sensitive minimizer signature: A collection of techniques for using hash functions to map large sets of objects/data items down to smaller hash values (minimizer signature or minhash values) in such a way that, when two objects/data items have a small distance from each other, their hash values are likely to be the same.

Maximum density cluster: Group of data items in a contiguous region with a high density separated from regions of low density of data items.

Referring now to the drawings, and more particularly to FIG. 1 through FIG. 6C, where similar reference characters denote corresponding features consistently throughout the figures, there are shown preferred embodiments and these embodiments are described in the context of the following exemplary system and/or method.

FIG. 1 illustrates an exemplary block of a system, for mapping read sequences using a pangenome reference, in accordance with some embodiments of the present disclosure. In an embodiment, the system 100 includes processor(s) 104, communication interface device(s), alternatively referred as or input/output (I/O) interface(s) 106, and one or more data storage devices or memory 102 operatively coupled to the processor(s) 104 and modules 108. The processor(s) 104 may be alternatively referred as one or more hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) 104 is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server or a centralized data lake used as source of input data by the system 100.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 102 further may include modules 108. In an embodiment, the modules 108 includes a failure prediction module 110, for implementing functions of the system 100. In an embodiment, the modules 108 can be an Integrated Circuit (IC) (not shown), external to the memory 102, implemented using a Field-Programmable Gate Array (FPGA) or an Application-Specific Integrated Circuit (ASIC). The names (or expressions or terms) of the modules of functional block within the modules 108 referred herein, are used for explanation and are not construed to be limitation(s). Further, the memory 102 can also include the repository 112. In an embodiment, the repository 112 includes a data source, which may be external or internal to the system 100. The data source may store the input data received from various external sources, wherein the input data includes a plurality of read sequences (r) and a genome variation graph (G). The memory 102 may further comprise information pertaining to input(s)/output(s) of each step performed by the system 100 and methods of the present disclosure.

The modules 108 includes a genome variation graph mapping module 110 for processing the read sequences received as input by constructing the subgraph by mapping each read sequence among the plurality of read sequences (r) with the genome variation graph. The disclosed method is further explained with reference to the accompanying diagrams using the system 100 in conjunction with FIG. 2 through FIG. 6C.

Figure 2:
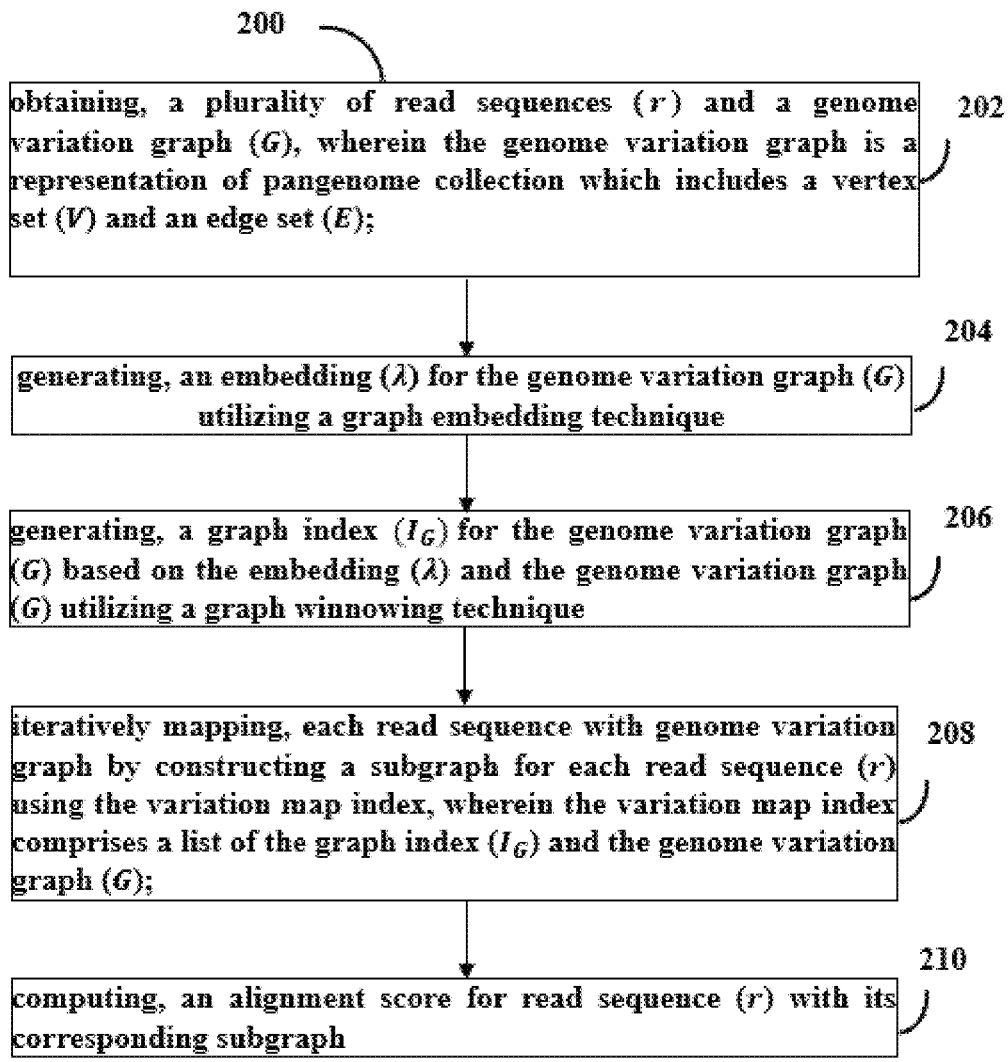
FIG. 2 is a flow diagram illustrating a method for mapping read sequences using a pangenome reference using the system of FIG. 1, in accordance with some embodiments of the present disclosure.

FIG. 2 is a flow diagram illustrating a method for mapping read sequences using a pangenome reference using the system of FIG. 1, in accordance with some embodiments of the present disclosure. The steps of the method 200 of the flow diagram will now be explained with reference to the components or blocks of the system 100 in conjunction with the example architecture of the system as depicted in FIG. 3 through FIG. 6C. In an embodiment, the system 100 comprises one or more data storage devices or the memory 102 operatively coupled to the one or more processors 104 and is configured to store instructions for execution of steps of the method 200 by the one or more processors 104. In an embodiment, the memory 102 store instructions for execution of steps of the method 200 by the one or more processors 104, for constructing the subgraph by mapping read sequences with the genome variation graph. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Figure 3:
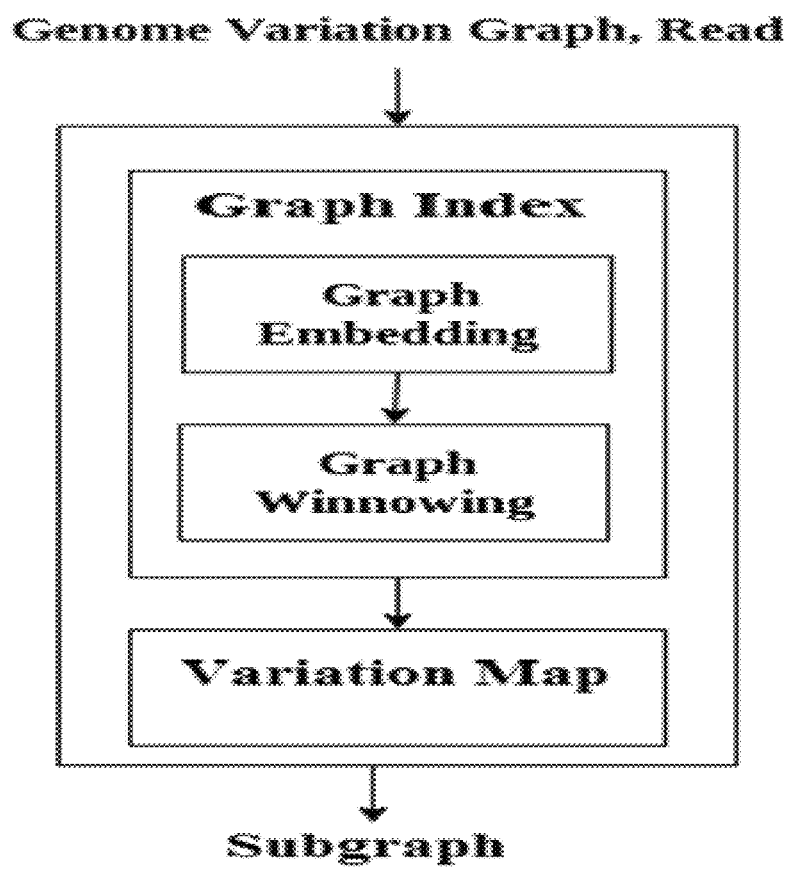
FIG. 3 illustrates a high-level architecture of the system of FIG. 1, in accordance with some embodiments of the present disclosure.

At step 202 of the method 200, the processor 104 is configured to obtain, the plurality of read sequences (r) and the genome variation graph (G), wherein the genome variation graph is a representation of pangenome collection which includes a vertex set (V) and an edge set (E). Referring now to FIG. 3, a high-level architecture of the system of FIG. 1, in accordance with some embodiments of the present disclosure. Here, the system 100 obtains the input data that includes the plurality of read sequences (r) and the genome variation graph (G) from the external sources, wherein the sources are obtained from one or more sequencing platforms. The sequencing platforms that includes as 1. Sequencing by Ligation: SOLiD, BGIseq, 2. Sequencing by Synthesis: Illumina—Miniseq, Hiseq, Miseq, Roche 454 (Pyrosequencing) Ion Torrent (Proton/PGM sequencing) 3. Long Reads: SMRT Oxford Nanopore (MinION, PromethION) Pacbio and 4. Synthetic Long Reads: 10X Genomics Illumina Synthetic Long Reads. Further, the genome variation graphs are constructed using pangenome sequences which contains human genome sequences and the variations together in a population generally collected and maintained by population sequencing projects started by various government and research organizations around the world like 1000 genomes project, million human genomes project and the like. Genome variation graphs can be constructed and extended for other species which can make use of pangenome sequences from a million veteran program, a million plant or animal genomes project, a million micro-ecosystem genomes projects and the like from any of the major genome collection initiatives. Further, the read sequence samples obtained as input are generated using sequencing technologies such as Oxford Nanopore Technology (ONT), Pacific Biosciences (PacBio) available in gene banks, gene databases and other available open ongoing genome projects across the world.

In one embodiment, the genome variation graph is the representation of pangenome collection which includes the vertex set (V) and the edge set (E). Here, the pangenome is the collection of genome sequences that can be utilized as a reference for mapping the read sequences. For example, a genetic information can be structured as a genome variation graph which stores multiple individuals or organisms. One way to represent the pangenome can be as a directed graph having a plurality of vertices and a plurality of edges. In such genome variation graph, genetic variations can be incorporated as a divergent paths along the graph. Genetic similarities can be represented as a single path. Genomic data such as nucleotide or protein sequences, may be associated with either the vertices or the edges of the graph. Thus, the genome variation graph can be either vertex-based or edge-based. Genome variation graphs can also be Multiple Sequence Alignment (MSA) graphs or any graph/s which can encode genome sequences as paths. Further, the received genome variation graph (G=V, E,l) is extended to connect with a directed acyclic graph with the vertex set (V) and the edge set (E) and vertex label $\ell$ (v) wherein for each (v∈V).

The edge set (E) is represented as an ordered pair from V×V, wherein '×' represents the cartesian product. The proposed disclosure is capable of processing various graph representations like adjacency lists, adjacency matrices and incidence matrices. Further an XML-based graph file formats like DOT files or a simple text-based formats like GFA files can be processed which are the most common graph representations can in the domain. Further, graphical fragment assembly file (GFA file) represents continuous sequence or subsequence as vertices and edges as links between the vertices with orientation and overlapping information. GFA files capture sequence graphs, assembly graphs and represent variations in genomes, splice graphs in genes, or even capture the overlap between reads from long-read sequencing technology. On the other hand, DOT (graphical description language) file DOT includes description about graphs and written using the DOT Language which is a simple text graph language that is used to interpret abstract representation of objects that is usually joined by links. In such DOT files, these objects represent vertices and edges which are referred as linked pairs.

At step 204 of the method 200, the processor 104 is configured to generate, an embedding ($\lambda$) for the genome variation graph (G) utilizing a graph embedding technique Referring now to FIG. 3, the graph embedding submodule of the system 100 processes the genome variation graph (G) for generating an embedding ($\lambda$) using the graph embedding technique. Considering an example referring now to FIG. 4A, for every possible non-empty sequence of A, T, G and C is a nucleotide sequence. Here, the plurality of read sequences (r) and the vertex labels $\ell$ (v) for every v in vertex set (V) are nucleotide sequences. Further, the set of all vertex labels $\ell$ (v) are nucleotide sequences represented as, {{C, A,T,A,T,T,A,G}, {T}, {T,G,T,G,A}, {C}, {A}, {T,T,G,T,G,A}}. Here, the graph embedding technique initially extracts the vertex set (V), the edge set (E), a vertex label $\ell$ (v) for every entity (v) of the vertex set (V) and a graph coordinate (v,i), where 'i' is the offset for a vertex label $\ell$ (v) from the genome variation graph (G). Consider, the below able 1 representing an example structure representing edge and vertices for the genome variation graph, the vertex set (V) is represented as V={1,2,3,4,5,6} for which the vertex label $\ell$ (v) is obtained for every entity (v) of the vertex set (V).

TABLE 1

Edge set and Vertex set of the example structure of genome variation graph

| Vertex Set (v) | Label $\ell$(v) | Edge set E of entity e (source vertex, destination vertex) |
|---|---|---|
| 1 | CATATTAG | (1, 2) |
| 2 | T | (1, 3) |
| 3 | TGTGA | (2, 3) |
| 4 | C | (3, 4) |
| 5 | A | (3, 5) |
| 6 | TTTGTG | (4, 6) |
|   |   | (5, 6) |

Figure 4A:
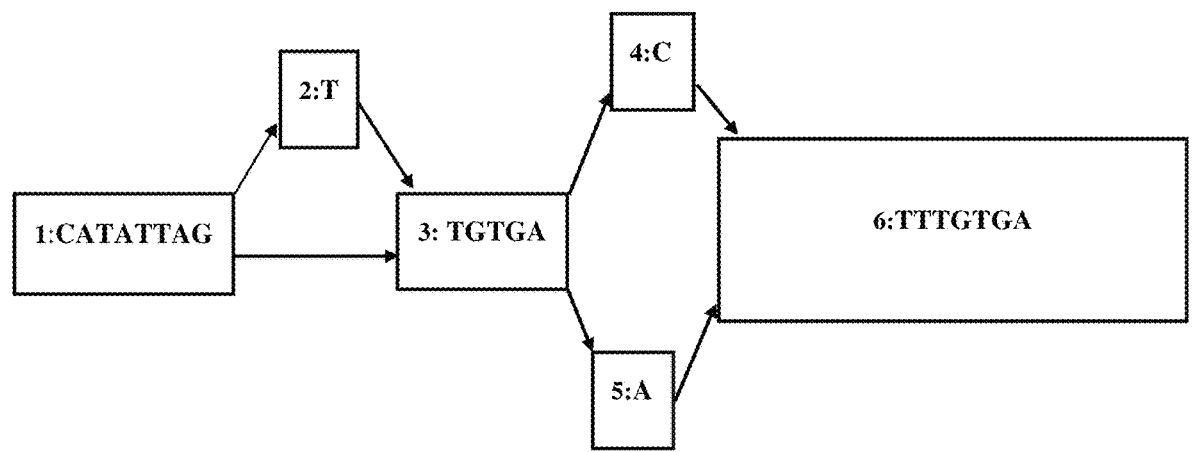
FIG. 4A illustrates an example structure of a genome variation graph utilized for mapping read sequences using the system of FIG. 1, in accordance with some embodiments of the present disclosure.
Figure 4B:
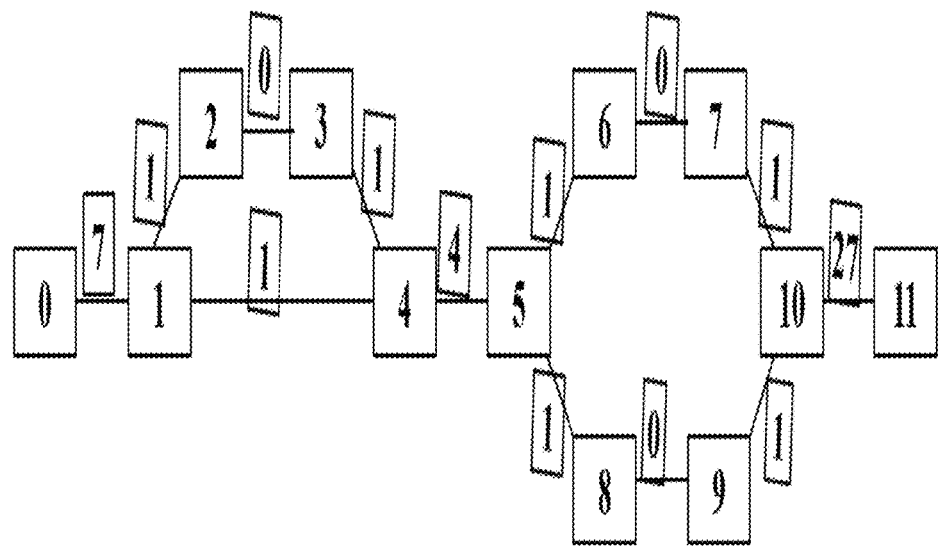
FIG. 4B illustrates an example structure of an auxiliary undirected weighted graph created from the genome variation graph using the system of FIG. 1, in accordance with some embodiments of the present disclosure.

Further, an auxiliary undirected weighted graph (G') is created using the genome variation graph (G). Referring now to FIG. 4B, a pair of vertices are included for each entity (v) of the vertex set (V) in the genome variation graph (G), wherein each pair of vertices includes a first element and a second element of the entity (v). The first element of the entity (v) and the second element of the entity (v) is connected with an undirected edge with a weight decremented with a predefined value represented as |$\ell$(v)|−1. The predefined value from the edge length of weight $\ell$ (v) is represented as 1. Further, for every entity in the edge e (source vertex, destination vertex) of the edge set (E), the second element of source vertex is fastened with the first element of destination vertex of the genome variation graph (G) with the predefined value of the weight. Further, the shortest path is computed from source vertex to the available vertices in the auxiliary undirected weighted graph (G'), wherein the source vertex is identified based on the first element having zero incoming edges in the genome variation graph (G).

TABLE 2

Edge set and Vertex set of the auxiliary undirected weighted graph created from the genome variation graph

| Vertex Set (V) | Vertex set V of entity 'v' (first element, second element) | Edge set E of entity e (first element, second element) | Weight $\ell$(v) − 1 | Edge set E of entity e (source vertex, destination vertex) | Weight |
|---|---|---|---|---|---|
| 1 | 0, 1 | (0, 1) | 7 | (1, 2) | 1 |
| 2 | 2, 3 | (2, 3) | 0 | (1, 4) | 1 |
| 3 | 4, 5 | (4, 5) | 4 | (3, 4) | 1 |
| 4 | 6, 7 | (6, 7) | 0 | (5, 6) | 1 |
| 5 | 8, 9 | (8, 9) | 0 | (5, 8) | 1 |
| 6 | 10, 11 | (10, 11) | 3 | (7, 10) | 1 |
|   |   |   |   | (9, 10) | 1 |

The graph embedding technique further computes the embedding ($\lambda$) for each graph coordinate (v,i) of the genome variation graph (G) based on the minimized shortest path distance to the first element and the second element of every entity v of the vertex set (V) in the auxiliary undirected weighted graph (G') as represented below in the equation 1, $$\lambda(<v,i>) = \min\{sp(v_1)+i, sp(v_2)+|\ell(v)|-i\} \quad \text{equation 1}$$

Here,

'$v_1$' and '$v_2$' are the first element and the second element of the vertex (v),

|$\ell$ (v)| is the length of the vertex label $\ell$ (v),

'sp' is the shortest path distance from the source vertex to the available vertices in the auxiliary undirected weighted graph (G')

'sp' (v1) is the shortest path distance from the source vertex to v1 in G'

'sp' (v2) is the shortest path distance from the source vertex to v2 in G'

At step 206 of the method 200, the processor 104 is configured to generate, a graph index ($I_G$) for the genome variation graph (G) based on the embedding ($\lambda$) and the genome variation graph (G) utilizing a graph winnowing technique. Referring now to FIG. 3, graph winnowing submodule of the system 100, a plurality of sequence winnow ($S_w$) paths for the genome variation graph (G) are obtained using a winnow length (w). Further, a path label is extracted for each path of the sequence winnow ($S_w$) by concatenating the vertex labels along the path based on the winnow length (w). The sequence winnowing ($h_w$) is computed for each path label based on the elements of the minimizer graph coordinates. Then, a set of distinct minimizer graph coordinates ($H_w$) is generated by performing sequence winnowing ($h_w$) for each path and then the graph index ($I_G$) is generated using the elements of the minimizer graph coordinates in ($H_w$), the embedding ($\lambda$) and a dictionary key (k).

In one embodiment, an index is created in the above manner by combining the results of graph winnowing and the graph embedding in a space efficient index for fast querying for read mapping with reduced time. Further, to identify regions in the graph where the plurality of read sequences (r) optimally align by performing graph winnowing technique on each of the read sequence (r). Further, the minimizers are looked up in the graph index IG. The hits from the graph index IG are then clustered in the embedded space to identify maximum density cluster. Here, each minimizer from the read sequence (r) occurs at multiple graph coordinates (Hw), the minimizer coordinates belonging to the constructed subgraph tend to cluster in the embedded space. Furthermore, the identified cluster from the minimizer hits to construct the subgraph where the plurality of read sequences (r) can be optimally aligned. Thus, nearby minimizers tend to cluster under this embedding. Different choices of embedding allow fast identification of the cluster ensuring the corresponding subgraph is sufficiently pruned.

The graph index (IG) winnows all the winnow length w length paths in genome variation graph (G) resulting the set of minimizer graph coordinates embedded into the integer based on the computed shortest path distance from a designated source vertex coordinate in an undirected version of the genome variation graph (G). These embeddings are stored against the minimizer values for generating the graph index (IG) using the elements of the minimizer graph coordinates in (Hw) the embedding (A) and a dictionary key (k). Here, we provide the bounds on the expected number of minimizers created by variation map for the genome variation graph (G). Specifically, the subgraph is constructed from a collection of (N) related random sequences each of length at most (n) wherein $C=\{S_1, \ldots, S_N\}$ The sequences in C are generated by a coupled random process, starting with a designated random sequence, random independent mutations with probability p are introduced to generate each of the remaining read sequences in C.

The collection C are generated from a coupled random process as described where a random sequence and a random independent mutations with probability p are introduced to generate each of the remaining sequences in C. This generation model is obtained from the mutation model approximations as proposed. Sequence $S_1$ also denoted as $S_1^*$, is designated as the basis sequence which is a random sequence where the nucleotide at each location is chosen independently and uniformly at random. Each remaining sequence $S_k$ for $k \in \{2, \ldots N\}$ are generated independently as gapped variant of the basis sequence $S_1$ using the following coupled process. The basis sequence $S_1^*$ is scanned sequentially from left to right for n steps. At each step t, the nucleotide present in $S_1^*$ is appended to $S_k$ independently with probability 1−p for some fixed p. With probability p, a gap introduced in $S_k$ either as a deletion from $S_1^*$ (i.e., skip the nucleotide in $S_1^*$), a random nucleotide substitution in $S_k$ or a nucleotide insertion in sk. In case of insertion, the scan location in $S_1^*$ does not change. It is straightforward to verify the given sequence from the collection C which is a random sequence where the nucleotide at each location is chosen independently and uniformly at random. However, any two sequences from the collection C are not independent of each other. If the mutation and gap probabilities are unequal, let p denote the maximum of them in the following analysis In one embodiment, the expected number of w length, the plurality of read sequences (r) is bounded by $(1+p(N-1))^w$. For the ease of exposition, it is generality that each vertex of the genome variation graph (G) has only single nucleotide label is considered. If the vertex (V) has longer label, it can be replaced by a corresponding path of single nucleotide vertices. Let the vertices along the $S_1$ path in the genome variation graph (G). be $U=\{u_1, \ldots, u_n\}$ and let $d_i$ be the out-degree of $u_i$. Let X denote the set of all w length path labels in G. Let $X_i$ for $i \in \{1, \ldots, n\}$ denote the subset of X where each path x in it has $u_i$ at location x[m−2]. Let R denote the remaining paths from X not included in any of $X_i$. Consider the m−1 length prefix x[0, . . . , m−2] of each path x from an $X_i$. Let $n_i$ be the number of distinct such prefixes from $X_i$. Clearly, $|X| \leq \Sigma n_i d_i + |R|$. Observing that $n_i$ is independent of $d_i$ and $d_i$ is upper bound by 1+Binomial(N−1,p) because each of $s_2, \ldots, S_N$ can introduce an outgoing edge at $u_i$ with probability p, we obtain $E(|X|) \leq (1+p(N-1))E(\Sigma n_i + |R|)$. Clearly $\Sigma n_i + |R|$ is no more than the number of w−1 length paths in G. Herein it may be observed that w−1 length prefix of each path x from R is distinct as the out-degree of a non U vertex (vertex at x[m−2]) is at most 1. Repeating the above argument and using the observation that the expected number of 1 length paths (i.e., total nucleotides) in G is at most n(1+p(N−1)), we finally obtain $E(X) \leq n(1+p(N-1))^w$.

For k-mer length k, we show the following theorem is proposed. Here, the k-mer length k, which can be represented in the below equation 2, where the expected number of minimizers for G is upper bound by, For k-mer length k, the expected number of minimizers for G is upper bound by equation 2, $$\frac{2n}{w-k}(1+p(N-1))^{w+1} \qquad \text{equation (2)}$$

for winnow length (w). The above equation represents the expected number of winnow length (w) for the genome variation graph (G) bounded from the above equation 2 where, n(1+p(N−1))w. Further, combining the above equation with the charging argument, which is an extension for the linear random sequences for the graph setting for obtaining the equation 2.

Theorem 1—The expected number of minimizers for G is bounded by $$\frac{2n}{w-k}(1+p(N-1))^{w+1}$$

for winnow length w.

To prove the above theorem, the expected number of w length paths in G is shown bounded from above by $n(1+p(N-1))^w$. Combining this with a charging argument, which is an extension of for linear random sequences to the graph setting to obtain the theorem.

The charging argument in for linear random sequences to our graph setting is extended. For a linear sequence s, a w sized window $W_i$ at coordinate i is charged, i.e., contributes a new minimizer k-mer say at s[j], if $W_i$ is the leftmost among the windows that overlap the k-mer at s[j] and the k-mer is a minimizer in them. It was shown in that this corresponds to the event that in the w+1 sized window W which is the union of $W_{i-1}$ and $W_i$, the minimizer of W is given by either its first k-mer or its last k-mer. The probability of this to happen in a random sequence is 2/(w+1). The total number of minimizers after winnowing an n length sequence s is then given by the total number of w length windows that are charged, which is 2n/(w+1).

Consider any w+1 length path in G. Let c' denote the w length suffix window of c and let x and x' denote the (minimizer) k-mers at locations h(c) and h(c') respectively. We charge window c' if and only if x is either the first or the last k-mer in c. It is straightforward to verify that each minimizer in G is charged to at least one w length path window in G. In the linear case, a minimizer is charged to exactly one window whereas the same minimizer could be charged to multiple windows in the case of graphs. This can only overestimate the desired count. Recalling the generation process of G, it is observed that any given w+1 length path c in G encodes a random sequence. Hence, its w length suffix c' is charged with probability 2/(w−k+2). The graph G has an underlying topology from $\Omega$ which denote the space of all graph topologies that can arise from the graph creation process described earlier. Each topology in $\Omega$ has a unique encoding where each vertex u has an associated distinct triplet id of the form <i, j, l> denoting that u is uniquely associated with the l length subsequence of $s_i \in \mathcal{C}$ starting from offset j. For a given topology, the specific vertex labels are still random. It is clear from the generation process that for any fixed topology T, the sequence for any given path in T is a random sequence. Hence, if $n_T$ denote the number of w+1 length paths for a topology T, a w+1 length path is charged in a graph with topology T with probability 2/(w−k+2). Let D denote the number of charged k+1 length σ-sequence in G. The total number of minimizers is upper-bound by D. We have $E(D|T)=2 \cdot n_T/(w-k+2)$. Hence, following equation 3 is obtained $$E(D) = \sum\nolimits^{T \in \Omega} E(D \mid T)Pr(T) = \quad \text{equation (3)}$$

$$\frac{2}{w-k+2} \sum\nolimits^{T \in \Omega} n_T Pr(T) \leq \frac{2n}{w-k}(1 + p(N-1))^{w+1}$$

where the last inequality follows by applying Lemma 2 as $\sum^{T \in \Omega} n_T Pr(T)$ is the expected number of w+1 length paths.

From the above theorem, it can be seen that for small mutation probability p, 5 the total minimizer size, which is the proof are provided as follows that are similar to the linear reference case, the number of minimizers on expectation, which is represented in equation 3, Similar to the linear reference case, in the worst case, the number of minimizers on expectation is represented in equation 4, $$O\left(\frac{n}{w}\exp(pwN)\right) \quad \text{equation (4)}$$

grows as 1/w fraction of the expected number of w length winnows in the genome variation graph (G).

Figure 5:
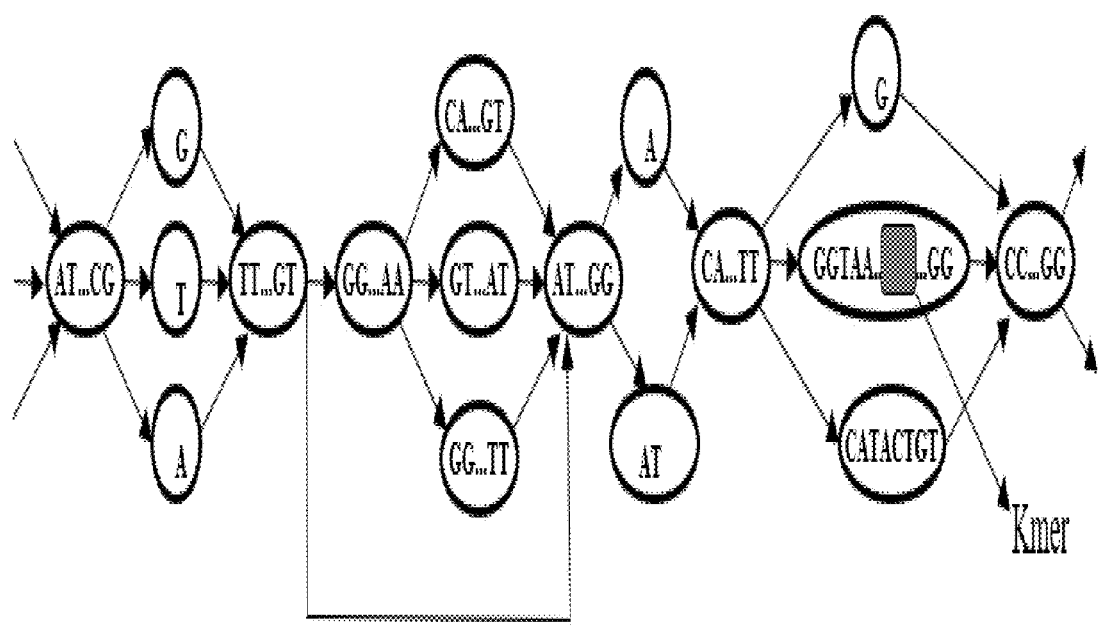
FIG. 5 illustrates a dense subgraph cascaded form of the genome variation graph using the system of FIG. 1, in accordance with some embodiments of the present disclosure.

Referring now to FIG. 5, for each minimizer k-mer, only the embedding of its corresponding graph coordinates in the genome variation graph G are stored in the graph index (IG), with the respective graph coordinates along with their embedding as described below in equation 5, $$IG[r]=\{\lambda | IG[r]\} \quad \text{equation (5)}$$

The graph index has an adjacency representation of the genome variation graph (G) sorted by the vertex embedding values. The adjacency list for each vertex is also stored as a sorted skip list or a sorted array. This allows efficient extraction of the subgraph constructed from the variation map for identifying the optimal gapped alignment of the plurality of read sequences (r) for constructing the subgraph.

At step 208 of the method 200, the processor 104 is configured to map iteratively, each read sequence to genome variation graph by constructing a subgraph using the variation map index, wherein the variation map index comprises a list of the graph index (IG) and the genome variation graph (G). Referring now to FIG. 3 and FIG. 5A, 5B, from the received plurality of read sequences (r) and the genome variation graph (G), the subgraph is constructed by computing a minimizer set (R) for each read sequence (r) by applying sequence winnowing (hw). The presence of the minimizer set (R) is identified in the graph index (IG). Further, a hitlist (H) is determined based on the presence of the minimizer set (R) identified in the graph index (IG) and then clustering the hitlist (H). The maximum density cluster is identified from a pair of predefined intervals (hl,hr) by sorting the hitlist H and then the subgraph is constructed based on the vertices whose embedding (λ) lies between the interval [l,r] using the maximum density cluster from the pair of predefined intervals (hl,hr) by applying a correction factor. The interval [l,r] is obtained from the maximum density cluster from the pair of predefined intervals (hl,hr) by applying a correction factor which is half of the length of the read sequence r, and the correction factor is subtracted from hl and the correction factor is added to hr.

In one embodiment for a read sequence (r), the mapper aims to efficiently construct the subgraph from the auxiliary undirected weighted graph (G') of the genome variation graph (G) where the read sequence (r) can align optimally. The alignment of the read sequence (r) can be performed with any of the existing sequence to graph alignment algorithms. The minimizer set (R) of the input read sequence (r) is first computed by applying the sequence winnowing (hw) on each read sequence (r). For each distinct minimizer k∈ R, the entries stored in the graph index (IG) are included in the hit set (H). The graph index (IG) contains the embedding (λ) for all the graph coordinates in the genome variation graph (G) where k, is the dictionary key. The graph index (IG) is assumed to be empty if the dictionary key (k) is not present as the minimizer in the genome variation graph (G) then clustering the hitlist (H). Further, a maximum cardinality is identified enclosing the interval [l,r] of fixed width covers the maximum number of elements in the hitlist (H). This can be done in O(|H|log|H|) time by linear scan sorting H. The interval width is fixed with the length f of the read sequence (r). Let hl be the left end and hr be the right end respectively of the final enclosing interval. The final graph region identified by the variation map given by the constructed subgraph induced in the vertices whose embedding (λ) lies between the interval [hl−$\ell$/2,hr+$\ell$/2]. The sorted adjacency representation in the variation map index allows efficient extraction of the constructed subgraph based on the variation map.

At step 210 of the method 200, the processor 104 is configured to compute, an alignment score for read sequence (r) with its corresponding subgraph.

FIG. 6 illustrates an example structure of dense subgraph with a cascade of the genome variation graph using the system of FIG. 1, in accordance with some embodiments of the present disclosure. The dense regions of the subgraph can lead to increased time and space requirements for V-MAP indexing as the number of possible winnow lengths w paths in these regions could be very large. The random sampling in such dense regions where, instead of considering all the winnow w length paths, M such paths are randomly sampled where M is a parameter. This helps in reducing the time and space requirements and at the same time maintain high mapping accuracy. Variation map indexing switches to random sampling mode for the graph coordinates when the total number of w length paths starting from that coordinate exceeds M. The final minimizer set of any graph under sampling is a subset of the minimizer set without sampling. The effect of random sampling on the minimizer set. The minimizers are due to sampling. Consider the k-mer in the genome variation graph (G). The expected analysis number of winnow length (w) path samples which has the minimizer (R). Let U={u1, . . . , ur} be the set of coordinates in the genome variation graph (G) such that x is reachable from them through a σ path of length at most (w). Let q be the probability that a random w length σ path sample from a randomly chosen (uniformly at random) u ∈U contains x. The number of w length in σ paths from each ui∈ U exceeds M. In the analysis, we assume that the k-mer in any w length σ paths are distinct which can be proven using the below mentioned Lemma.

Lemma—The expected number of path samples each having x as the minimizer≥qM.

Proof: Considering that |U|≥w−k+1|U| least w−k+1 graph coordinates lying on some w length for each path leading to x in the genome variation graph (G). Consider any graph coordinates. Let p denote the probability that a random w length path sample from ui contains the k-mer x. Then, the probability that a random sampled path contains x as minimizer is at least $\alpha_i/(w-k+1)$. The total number of path samples (with repetition) from all of u1, . . . , ur is rM. In this sampling, let Z denote the expected number of path samples where each of them have x as a minimizer. We have Z≥M (w−k+1) Pr i=1i. Recalling that r≥w−k+1, we obtain that $$Z \geq \frac{M}{r} \sum_{i=1}^{r} \alpha i = qMJ.$$

It is straightforward to see that, under no sampling, the 10 expected number of w length paths in G each having x as minimizer is S/(w k+1), where S denote the total number of w length paths from all the coordinates in U where each path contains the k-mer x. From the above lemma, we infer that when a minimizer k-mer x of graph G is present in a dense region with high q value, then with a suitable sampling parameter M, sufficiently many paths under sampling also have x as a minimizer on expectation. It shows part of a commonly occurring dense subgraph topology which is a cascade of variations. The number of w length paths from a fixed graph coordinate grows by a multiplicative factor depending on the number of cascade elements it can pass through. For the k-mer x as shown in the subgraph, there are several w length paths from every coordinate in U. However, a random path sample from any coordinate in U will pass through the vertex containing x with probability 1/3, implying a higher q value.

Figure 6A:
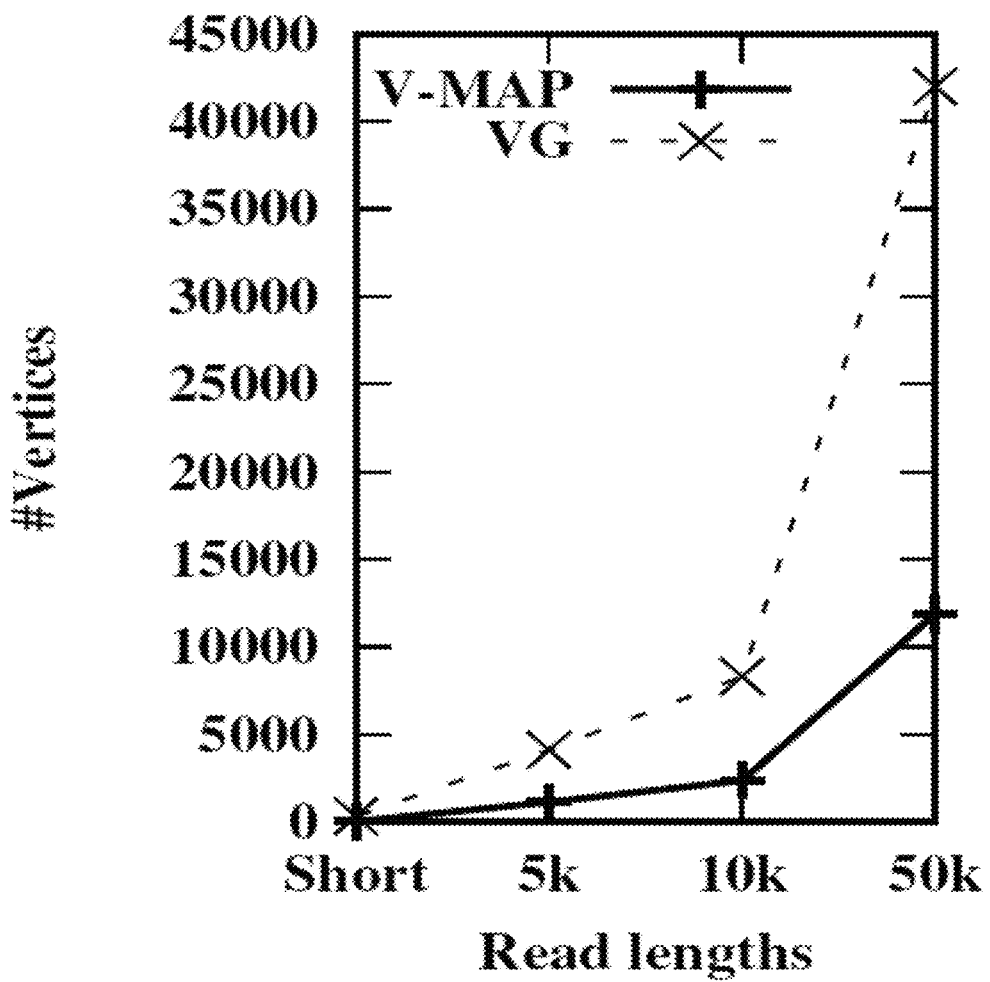
FIG. 6A illustrates graphical representation of read lengths versus vertices for the constructed subgraph by mapping read sequences with genome variation graphs using the system of FIG. 1, in accordance with some embodiments of the present disclosure.

FIG. 6A illustrates graphical representation of read lengths versus vertices for the constructed subgraph by mapping read sequences with genome variation graphs using the system of FIG. 1, in accordance with some embodiments of the present disclosure. The number of vertices and the total number of nucleotides in the vertex label sequences of the subgraph. The reduced subgraph sizes significantly improve the gapped alignment time. The difference in alignment time between the two tools can be attributed to the smaller subgraphs identified by variation map for the alignment phase. The improved algorithm and implementations for gapped alignment on subgraph improves overall time. Various experiments performed on the proposed disclosure measuring mapping accuracy and run time performance for the variation map (genome variation graph mapping module or V-MAP). The variation map (V-MAP) was compared with the state-of-the-art a VG mapper (VG), a popular linear, a reference mappers BWA-MEM and a Minimap2.

Experimental Results:

In one embodiment, mapping experiments were performed using real and simulated short or long read sequence (read) datasets on the graph constructed from the 1000 genomes variation data. The variation data contained about 85 million variations and the resulting variation graph consists of about 3×108 vertices and 4×108 edges. The 1000 genomes variation graph is a directed acyclic graph. The performance of V-MAP with the state-of-the-art graph-based read mapper variation graph and the popular linear reference mappers BWA-MEM and Minimap2. Variation map index has 20 GB size and is constructed in just 2 hours using 16 GB RAM, which is significantly smaller than VG in terms of the time/resource requirements. In terms of the final alignment score, variation map achieved higher alignment scores for a significantly large fraction of long reads. The performance was also significantly better than the linear mappers. Also, variation map V-MAP accuracy in identifying the target region were 96.6% and 99% for short and long reads respectively. V-MAP identifies the target subgraph in milliseconds, even for long reads. In contrast to the whole graph size, the subgraph sizes were significantly smaller and were proportional to the read lengths. This led to a significant reduction in time for gapped alignment time of reads to target subgraphs. The disclosure provides analytical bounds for the V-MAP index size and for the V-MAP path sampling approach while indexing dense graph regions. In one embodiment, the experimental results human reference genome GRCh37 and the 1000 Genomes variation data were used to construct a Human genome graph for our experiments. The variation data consist of about 85 million variations. The VG graph construction tool was used with default parameter setting to construct the reference graph. The reference graph consisted of about 3.2×108 vertices and 4.1×108 edges in total. The plurality of read sequences (r) were experimented using a Illumina tool, a PacBio pool and a ONT real reads of Ashkenazim Trio HG002_NA24385_son made available by Genome In A Bottle (GIAB) Consortium were used. Around 104 reads of average length 117 formed the Illumina readset. For PacBio, 104 reads of length 5 k or above were used. For ONT, about 8000 reads were available in the GIAB dataset with read length 1000 or above. Simulated read sequences were also used in the experiments. Reads were generated using read simulation tools from sequences arising from random paths in the reference graph. The ART tool was used to generate Illumina short reads of lengths in the range 100 to 200 with its default error profile. PacBio and Nanopore (ONT) long reads of average lengths of 5 k, 10 k and 50 k were generated using the ReadSim tool. In total, 144×105 short reads and 3.8×105 long reads were generated. All reads in the read set are from forward strand.

Figure 6B:
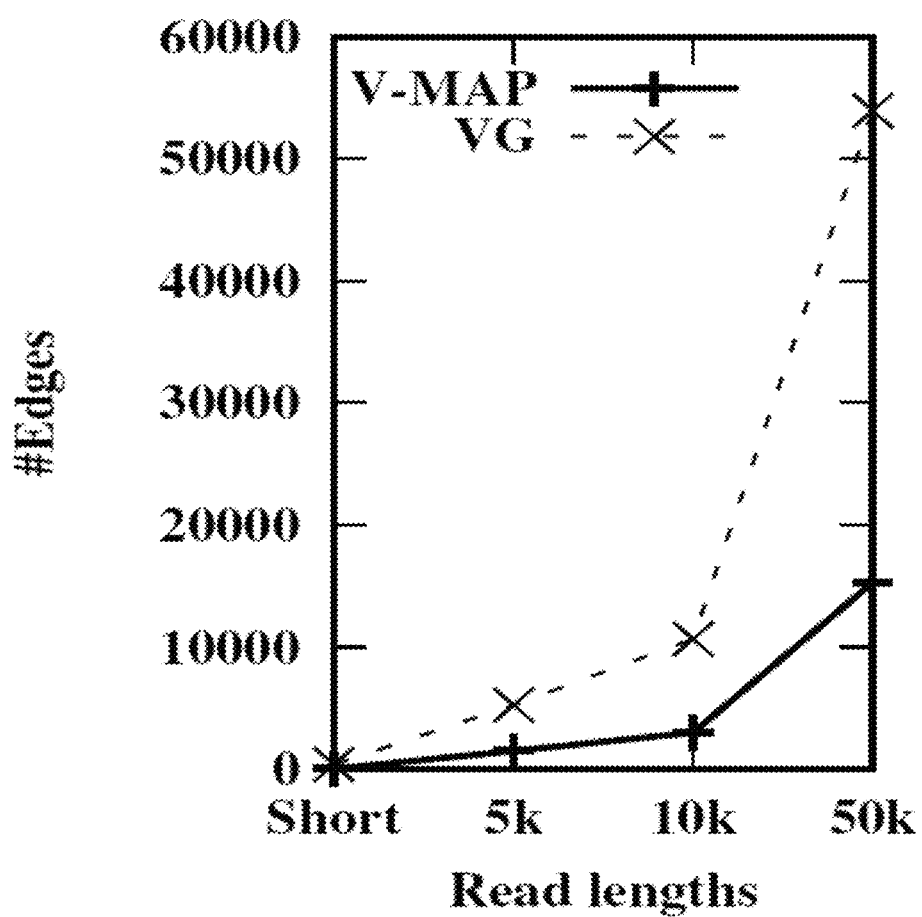
FIG. 6B illustrates graphical representation of read lengths versus edges for the constructed subgraph by mapping read sequences with genome variation graphs using the system of FIG. 1, in accordance with some embodiments of the present disclosure.

FIG. 6B illustrates graphical representation of read lengths versus edges for the constructed subgraph by mapping read sequences with genome variation graphs using the system of FIG. 1, in accordance with some embodiments of the present disclosure. The figure shows the number of edges, vertices and the total number of nucleotides in the vertex label sequences of the subgraph. The implementation details and the experimental results where the read sequences were the index construction and mapping were performed on 200 GB RAM linux machine with 48 threads and with 6 TB HDD. Choices for the variation map parameters w and k were determined by a grid search based on the mapping accuracy on a separate set of random reads. Values w=35, k=20 were chosen for short reads and w=40, k=20 were chosen for long reads (PacBio/ONT). The random sampling parameter M for indexing was set to 30,000. The final alignment score achieved by the candidate methods V-MAP, VG, BWA-MEM, and Minimap2 were measured for the real read set. In V-MAP, as in VG, the GSSW graph-based aligner were used to compute the gapped alignment score to the identified subgraph. The default alignment score parameters of BWA-MEM for gap open, gap extension, match, and mismatch were used across all tools. Table 3 gives the percentage of reads where each tool was a top scorer.

TABLE 3

Comparison of the candidate methods based on the final alignment scores achieved. The best performance among BWA-MEM and Minimap2 is shown under linear mapper

| Illumina | | PacBio | | ONT | |
|---|---|---|---|---|---|
| Variation map | VG | Variation map | VG | Variation map | VG |
| 0.0004 | 0.05 | 5.85 | 3.29 | 7.06 | 6.42 |

That is, its score is no less than the score of other tools. The best value among BWA-MEM and Minimap2 is shown under the linear mapper column. The low percentage for linear mapper especially for long reads can be attributed to the fact that unlike the graph-based mappers, linear mappers must work with only the linear reference and without any variant information. The graph mappers like variation map, on the other hand achieve higher alignment score by working on a unified space of reference and variations encoded as a graph. The purpose of including the linear mappers in the comparison is only to bring out the advantage of using a pangenome reference over a linear reference and not to highlight the performance of any specific linear mapper.

Figure 6C:
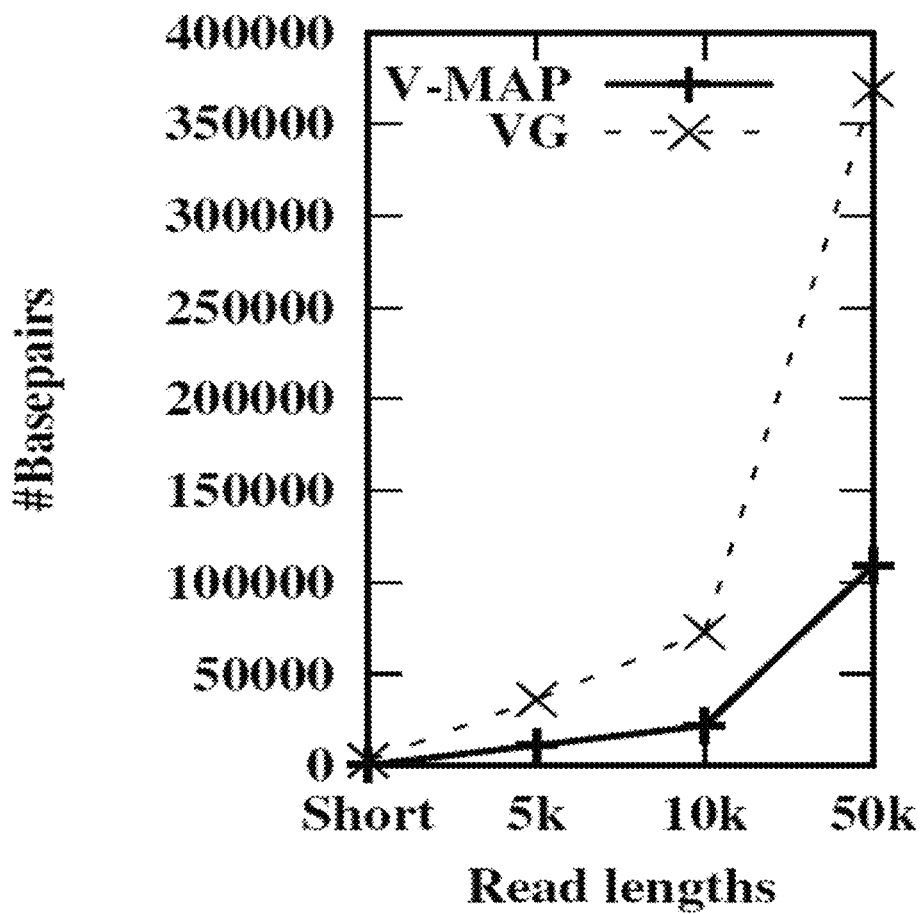
FIG. 6C illustrates graphical representation of read lengths versus base pairs for the constructed subgraph constructed by mapping read sequences with genome variation graphs using the system of FIG. 1, in accordance with some embodiments of the present disclosure.

FIG. 6C illustrates graphical representation of read lengths versus base pairs for the constructed subgraph constructed by mapping read sequences with genome variation graphs using the system of FIG. 1, in accordance with some embodiments of the present disclosure. The figure shows the number of base pairs and the total number of nucleotides in the vertex label sequences of the subgraph. The table 2, shows the average percentage gain in the alignment score achieved respectively by V-MAP and VG for reads where they were top scorers. As seen in table 4, the percentage gain is pronounced in the case of long reads.

TABLE 4

Average percentage gain in the alignment score for V-MAP and VG

| | Illumina | | | PacBio | | | ONT | | |
|---|---|---|---|---|---|---|---|---|---|
| % read sequences | Variation map | VG | Linear mapper | Variation map | VG | Linear mapper | Variation map | VG | Linear mapper |
| Top scorer | 95.28 | 99.79 | 87.98 | 81.15 | 52.01 | 3.2 | 80.73 | 62.43 | 3.43 |

In one embodiment, using the simulated reads, the mapping accuracy is calculated and measured as the fraction of read sequences(r) for which the subgraph is constructed by the mapper contained the path in the graph from which the read was generated.

TABLE 5 shows the mapping accuracy of variation map (V-MAP) and VG

| Read class | 100 | 150 | 200 | Pac 5k | Pac 10k | Pac 50k | ONT 5k | Pac 10k | Pac 50k |
|---|---|---|---|---|---|---|---|---|---|
| V-MAP | 95.22 | 96.21 | 98.49 | 96.90 | 99.04 | 99.63 | 99.47 | 99.57 | 99.95 |
| VG | 99.67 | 99.80 | 99.98 | 71.62 | 70.48 | 71.27 | 94.28 | 94.13 | 93.93 |

V-MAP exhibits consistently superior performance for long reads with a much smaller index. In addition to higher accuracy, V-MAP also achieved considerably higher final alignment score. The average score difference was in excess of 680 for reads in the 5 k to 10 k range and 3590 for 10 k to 50 k range and 18300 for above 50 k length reads. For short reads, the V-MAP alignment score was less than VG by 2 on average. In a related experiment of mapping 24 k simulated reads of length 10 k each from the graph with no sequencing errors, V-MAP achieved full alignment score for all but 2 reads in comparison to 96.8% of the reads for VG. In one embodiment, mapping performance Table 6 provides the indexing performance such as an index construction time, an index size, an intermediate storage and a RAM requirements for the V-MAP and VG.

TABLE 6

Index construction and Mapping performance

| Index Parameters | VG | V-MAP |
|---|---|---|
| Construction Time | 36 hours | 2 hours |
| Intermediate storage | ~2 TB | 0 |
| Index Size | 80 GB | 21 GB (short reads) 18 GB (long reads) |
| RAM | 200 GB | 16 GB |
| # indexing threads | 32 | 4 |
| Mapping RAM | 75 GB | 27 GB |

Further, Table 7 provides the average read mapping time (single thread) for V-MAP and VG for short reads and long reads. Map time is the subgraph identification time. Align time is the time to perform gapped alignment of the read to subgraph using GSSW.

TABLE 7

Map and align timings

| | Map time (ms) | | Align time (ms) | | Total time (ms) | |
|---|---|---|---|---|---|---|
| Read Length | Variation map | VG | Variation map | VG | Variation map | VG |
| 100 | 0.45 | 4.56 | 1.88 | 33 | 2.33 | 37.56 |
| 150 | 0.67 | 12.02 | 2.94 | 94.85 | 3.61 | 106.87 |
| 200 | 1.24 | 37.5 | 3.91 | 153.15 | 5.15 | 190.65 |
| 5k | 5.84 | 144.16 | 540.28 | 4300.22 | 546.12 | 4444.39 |
| 10k | 11.35 | 292.22 | 1831.34 | 9010.63 | 1842.69 | 9302.85 |
| 50k | 63.63 | 1223.1 | 39584.69 | 48652.42 | 39648.13 | 49875.5 |

The map time is the subgraph identification time and align time is the time taken for gapped alignment of the read to the identified subgraph using the GSSW graph-based aligner.

The written description describes the subject matter herein to enable any person skilled in the art to make and use the embodiments. The scope of the subject matter embodiments is defined herein and may include other modifications that occur to those skilled in the art. Such other modifications are intended to be within the scope of the present disclosure if they have similar elements that do not differ from the literal language of the embodiments or if they include equivalent elements with insubstantial differences from the literal language of the embodiments described herein.

The embodiments of the present disclosure herein address the challenging problem of mapping read sequences with genome variation graph. The disclosed method is a low-cost, efficient, accurate and scalable system for mapping read sequences with large genome variation graphs. The proposed disclosure provides an efficient construction of the subgraph from the genome variation graphs, wherein the read sequences align optimally. The proposed disclosure is a memory efficient system as its index is compact and is constructed using a novel approach of graph winnowing, path sampling and embedding. Further, the system is efficient in using all important k-mers in the read sequence for subgraph construction using a novel approach that combines graph winnowing technique and the graph embedding technique with improved performance with faster results. Also, graph winnowing technique combined with the graph embedding technique reduces number of signature lookups and leads to fewer isolated false matches of the read sequence signatures, thereby achieving faster clustering. The proposed disclosure is a robust read sequence mapping technique which is independent of the input read sequence lengths and the sequencing technology. This enables to handle both forward and reverse complement read sequences, allows dynamic updates to the index where new vertices and the new edges were added to the genome variation graph. Further, the system can easily be integrated or plugged with any existing tools which supports sequence to graph based gapped aligners. The system can analyze various components of the genome variation graph by providing a feature to consider special parts of interest from the graph (chromosomes/contigs/exons) for humans and other species. The proposed disclosure also supports multiple input formats such as gfa, dot and other possible graph adjacency representations and supports generation of graph-based alignment mapping output (GAM) format to plugin or verify the alignment scores for further variant analysis and can be extended to other graph alignment output formats.

In one embodiment the proposed system can be extended to many applications such as support to generic graphs (or) different graph formats which include cycles. The proposed disclosure can be extended to support mapping of paired-end and split read sequences. This method is further explored to include different graph embeddings for improving the variation map with improved accuracy and performance. For instance, an embedding in N2 could possibly lead to a finer graph pruning and hence faster alignment with marginal increase in clustering time and index size of the graph. The variation map provides a pipeline for pangenome analysis to detect novel and other variants by plugging-in with any of the graph-based gapped aligners. Pipeline can eventually rise applications such as population-wise studies, sub-population studies, RNA-sequence analysis, Rare disease/Cancer/Diabetes analysis, analysis of disease vs healthy conditions, developing personalized medicine, microbial analysis and plant and animal genomics.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

The invention claimed is:

1. A processor implemented method for mapping read sequences with a genome variation graph comprising:
obtaining a plurality of read sequences (r) and a genome variation graph (G), wherein the genome variation graph is a representation of pangenome collection which includes a vertex set (V) and an edge set (E);
generating an embedding ($\lambda$) for the genome variation graph (G) utilizing a graph embedding technique;
generating a graph index (IG) for the genome variation graph (G) based on the embedding ($\lambda$) and the genome variation graph (G) utilizing a graph winnowing technique in a space efficient index for fast querying for read mapping with reduced time, wherein generating the graph index (IG) for the genome variation graph (G) based on the embedding ($\lambda$) and the genome variation graph (G) utilizing the graph winnowing technique comprises:
obtaining a plurality of sequence winnow ($S_w$) paths for the genome variation graph (G) using a winnow length (w);
extracting a path label for each path of the sequence winnow ($S_w$) by concatenating the vertex labels along the path based on the winnow length (w);
computing sequence winnowing ($h_w$) for each path label based on the elements of the minimizer graph coordinates;
generating a set of distinct minimizer graph coordinates ($H_w$) by performing sequence winnowing ($h_w$) for each path; and
generating the graph index (IG) using the elements of the minimizer graph coordinates in ($H_w$), the embedding ($\lambda$) and a dictionary key (k);
iteratively mapping each read sequence to the genome variation graph by constructing a subgraph for each read sequence (r) using the variation map index, wherein the variation map index comprises a list of the graph index (IG) and the genome variation graph (G); and
computing an alignment score for each read sequence (r) with its corresponding subgraph, wherein the subgraph with reduced graph size and proportional to a read length, reduces time for gapped alignment of the read sequences to the corresponding subgraphs.

2. The method as claimed in claim 1, wherein generating the embedding ($\lambda$) for the genome variation graph (G) utilizing the graph embedding technique comprises:
extracting each entity (v) from the vertex set (V), the edge set (E), a vertex label $\ell$ (v) for each entity(v) and a graph coordinate (v,i), where i is the offset for vertex label $\ell$ (v) from the genome variation graph (G);
creating an auxiliary undirected weighted graph (G') using the genome variation graph (G) by,
including a pair of vertices for each entity (v) of the vertex set (V) in the genome variation graph (G), wherein each pair of vertices includes a first element and a second element of the entity (v);
connecting the first element and the second element of each entity (v) with an undirected edge length of weight l decremented with a predefined value, wherein l is the length of the vertex label $\ell$ (v) in the genome variation graph (G);
fastening for every entity (e) of the edge set (E), the second element of a source vertex with the first element of a destination vertex of the genome variation graph (G) with a weight;
computing the shortest path from the source vertex to the available vertices of the auxiliary undirected weighted graph (G'), wherein the source vertex is identified based on the first element having zero incoming edges in the genome variation graph (G); and
generating an embedding ($\lambda$) for the graph coordinates where the distances between the graph coordinates are based on the shortest path distances of the graph coordinates where the shortest path distance for each graph coordinate (v,i) of the genome variation graph (G) is based on the minimized shortest path distance to the first element and the second element of the vertex set (V) in the auxiliary undirected weighted graph (G').

3. The method as claimed in claim 1, wherein the dictionary key (k) is the k-mer at the minimizer graph coordinates.

4. The method as claimed in claim 1, wherein the variation map index is constructed by combining the graph index ($I_G$) and the sorted genome variation graph (G).

5. The method as claimed in claim 1, constructing the subgraph for each read sequence (r) using the variation map index comprises:
   computing a minimizer set (R) for each read sequence (r) by applying sequence winnowing ($h_w$);
   identifying the presence of the minimizer set (R) in the graph index ($I_G$);
   determining a hitlist (H) based on the presence of the minimizer set (R) identified in the graph index ($I_G$) and then clustering the hitlist (H) based on their embedding;
   identifying a maximum density cluster based on the embedding and the hitlist H; and
   constructing the subgraph based on the vertices whose embedding (λ) lies in a bounded region around the maximum density cluster after applying a correction factor.

6. The method as claimed in claim 5, wherein the bounded region is obtained from the maximum density cluster by applying a correction factor based on the length of the read sequence (r).

7. The method as claimed in claim 1, wherein the alignment score for read sequence (r) with its corresponding subgraph is computed using any graph based gapped aligner methods.

8. A system for mapping read sequences with a genome variation graph, the system comprising:
   a memory storing instructions;
   one or more Input/Output (I/O) interfaces;
   and one or more hardware processors coupled to the memory via the one or more I/O interfaces, wherein the one or more hardware processors are configured by the instructions to:
      obtain a plurality of read sequences (r) and a genome variation graph (G), wherein the genome variation graph is a representation of pangenome collection which includes a vertex set (V) and an edge set (E);
      generate an embedding (λ) for the genome variation graph (G) utilizing a graph embedding technique;
      generate a graph index (IG) for the genome variation graph (G) based on the embedding (λ) and the genome variation graph (G) utilizing a graph winnowing technique in a space efficient index for fast querying for read mapping with reduced time, wherein generating the graph index (IG) for the genome variation graph (G) based on the embedding (λ) and the genome variation graph (G) utilizing the graph winnowing technique comprises:
         obtaining a plurality of sequence winnow ($S_w$) paths for the genome variation graph (G) using a winnow length (w);
         extracting a path label for each path of the sequence winnow ($S_w$) by concatenating the vertex labels along the path based on the winnow length (w);
         computing sequence winnowing ($h_w$) for each path label based on the elements of the minimizer graph coordinates;
         generating a set of distinct minimizer graph coordinates ($H_w$) by performing sequence winnowing ($h_w$) for each path; and
         generating the graph index (IG) using the elements of the minimizer graph coordinates in ($H_w$), the embedding (λ) and a dictionary key (k);
      iteratively map each read sequence (r) to the genome variation graph by constructing a subgraph for each read sequence (r) using the variation map index, wherein the variation map index comprises a list of the graph index (IG) and the genome variation graph (G); and
      compute an alignment score for each read sequence (r) with its corresponding subgraph, wherein the subgraph with reduced graph size and proportional to a read length, reduces time for gapped alignment of the read sequences to the corresponding subgraphs.

9. The system as claimed in claim 8, wherein generating the embedding (λ) for the genome variation graph (G) utilizing the graph embedding technique comprises:
   extracting the vertex set (V), the edge set (E), a vertex label ℓ (v) for every entity (v) of the vertex set (V) and a graph coordinate (v,i), where i is the offset for vertex label ℓ (v) from the genome variation graph (G);
   creating an auxiliary undirected weighted graph (G') using the genome variation graph (G) by,
      including a pair of vertices for each entity (v) of the vertex set (V) in the genome variation graph (G), wherein each pair of vertices includes a first element and a second element of the entity (v);
      connecting the first element of the entity (v) and the second element of the entity (v) with an undirected edge length of weight (l) decremented with a predefined value, wherein l is the length of the vertex label ℓ (v) in the genome variation graph (G);
   fastening for every entity (e) of the edge set (E), the second element of a source vertex with the first element of a destination vertex of the genome variation graph (G) with a weight;
   computing the shortest path from the source vertex to the available vertices of the auxiliary undirected weighted graph (G'), wherein the source vertex is identified based on the first element having zero incoming edges in the genome variation graph (G); and
   generating an embedding for the graph coordinates where the distances between the graph coordinates are based on the shortest path distances of the graph coordinates where the shortest path distance for each graph coordinate (v,i) of the genome variation graph (G) is based on the minimized shortest path distance to the first element and the second element of the vertex set (V) in the auxiliary undirected weighted graph (G').

10. The system as claimed in claim 8, wherein the dictionary key (k) is the k-mer at the minimizer graph coordinates.

11. The system as claimed in claim 8, wherein the variation map index is constructed by combining the graph index ($I_G$) and the sorted genome variation graph (G).

12. The system as claimed in claim 8, constructing the subgraph for each read sequence (r) using the variation map index comprises:
   computing a minimizer set (R) for each read sequence (r) by applying sequence winnowing ($h_w$);
   identifying the presence of the minimizer set (R) in the graph index ($I_G$);

determining, a hitlist (H) based on the presence of the minimizer set (R) identified in the graph index ($I_G$) and then clustering the hitlist (H) based on their embedding;

identifying a maximum density cluster based on the embedding and the hitlist H; and constructing the subgraph based on the vertices whose embedding ($\lambda$) lies in a bounded region around the maximum density cluster after applying a correction factor, wherein the bounded region is obtained from the maximum density cluster by applying a correction factor based on the length of the read sequence r.

13. The system as claimed in claim 8, wherein the alignment score for read sequence (r) with its corresponding subgraph is computed using any graph based gapped aligner methods.

14. One or more non-transitory machine-readable information storage mediums comprising one or more instructions which when executed by one or more hardware processors perform actions comprising:

obtaining a plurality of read sequences (r) and a genome variation graph (G), wherein the genome variation graph is a representation of pangenome collection which includes a vertex set (V) and an edge set (E);

generating an embedding ($\lambda$) for the genome variation graph (G) utilizing a graph embedding technique;

generating a graph index (IG) for the genome variation graph (G) based on the embedding ($\lambda$) and the genome variation graph (G) utilizing a graph winnowing technique in a space efficient index for fast querying for read mapping with reduced time, wherein generating the graph index (IG) for the genome variation graph (G) based on the embedding ($\lambda$) and the genome variation graph (G) utilizing the graph winnowing technique comprises:

obtaining a plurality of sequence winnow ($S_w$) paths for the genome variation graph (G) using a winnow length (w);

extracting a path label for each path of the sequence winnow ($S_w$) by concatenating the vertex labels along the path based on the winnow length (w);

computing sequence winnowing ($h_w$) for each path label based on the elements of the minimizer graph coordinates;

generating a set of distinct minimizer graph coordinates ($H_w$) by performing sequence winnowing ($h_w$) for each path; and generating the graph index (IG) using the elements of the minimizer graph coordinates in ($H_w$), the embedding ($\lambda$) and a dictionary key (k);

iteratively mapping each read sequence to the genome variation graph by constructing a subgraph for each read sequence (r) using the variation map index, wherein the variation map index comprises a list of the graph index (IG) and the genome variation graph (G); and computing an alignment score for each read sequence (r) with its corresponding subgraph, wherein the subgraph with reduced graph size and proportional to a read length, reduces time for gapped alignment of the read sequences to the corresponding subgraph.

* * * * *